United States Patent [19]

Geoghegan

[11] Patent Number: 5,298,135
[45] Date of Patent: Mar. 29, 1994

[54] PRODUCTION OF ELECTROPHORETICALLY-HOMOGENOUS PROTEIN-COLLOIDAL GOLD COMPLEXES

[75] Inventor: William D. Geoghegan, Houston, Tex.

[73] Assignee: Board of Regents, The University of Texas System, Austin, Tex.

[21] Appl. No.: 909,409

[22] Filed: Jul. 7, 1992

[51] Int. Cl.$^5$ ............................................. C25B 7/00
[52] U.S. Cl. .............................. 204/182.8; 204/182.9; 436/525
[58] Field of Search ........................... 204/182.8, 182.9; 436/525

[56] References Cited

FOREIGN PATENT DOCUMENTS 0165633 12/1985 European Pat. Off. .
02082 9/1991 PCT Int'l Appl. .

OTHER PUBLICATIONS

Geoghegan et al., "Passive Gold Agglutination, an Alternative to Passive Hemagglutination", Journal of Immunological Methods, 34 (1980) 11–21.
Baschong, et al., "Thiocyanate Gold: Small (2–3 nm) Colloidal Gold For Affinity Cytochemical Labeling In Electron Microscopy," Histochemistry, 83:409–411 (1985), published in Netherlands.
Harrison, et al., "Electrophoresis of Gold and Silver Particles," J. Chem. Soc., 775:3838 (1959), published in United Kingdom.
Murray, et al., "Factors Affecting the Rate of Removal of Gelatin-Stabilized Radiogold Colloid from the Blood," J. Lab. Clin. Med., 46:263–269 (1955), published in USA.
Murray, et al., "Interaction of Gelatin-Stabilized Radiogold Colloid and Plasma Proteins," Proc. Soc. Exp. Biol. Med., 91:252–255 (1955), published in USA.
Simon, N., "Radioactive Gold in Filter Paper Electrophoresis Patterns of Plasma," Science, 119:95 (1954), published in USA.
Slot, et al., "Sizing of Protein A-Colloidal Gold Probes for Immunoelectron Microscopy," J. Cell. Biol., 90:533–536 (1981), published in USA.
Geoghegan, et al., "The Electrophoretic Mobility of Protein Colloidal Gold Complexes," Proceedings of the Histochemical Society, p. 939, Abst. #51 (Mar. 29, 1989), published in USA.
Slot, et al., "A New Method of Preparing Gold Probes for Multiple-Labeling Cytochemistry," Eur. J. Cell. Biol., 38(1):87–93 (1985), published in Europe.
Dialog Search Report, printed in USA.
Geoghegan, "An Electrophoretic Method for Selection of Conditions for Production of Electrophoretically Uniform Protein Colloidal Gold Complexes," J. Histochem. and Cytochem., 39(1):111–121 (1991), published in USA.
Heard, et al., "The Characterization of Ag Sols by Electron Microscopy, Optical Absorption, and Electrophoresis," J. Colloid and Interface Sci., 93(2):545–555 (1983), published in USA.

Primary Examiner—John Niebling
Assistant Examiner—C. Delacroix-Muirheid

[57] ABSTRACT

A method is provided to determine the conditions required for the production of homogeneous protein-colloidal gold complexes. The method uses the electrophoretic migration of a discrete fraction of a sample of protein-colloidal gold complexes to identify, and produce homogeneous complexes. Further, the methods provided are used to select the pH of adsorption and the quantity of protein required to produce homogeneous complexes.

17 Claims, 9 Drawing Sheets

PRODUCTION OF ELECTROPHORETICALLY-HOMOGENOUS PROTEIN-COLLOIDAL GOLD COMPLEXES

The present invention is a continuation of U.S. Ser. No. 07/501,534, filed Mar. 28, 1990, now abandoned.

BACKGROUND OF THE INVENTION

During the last decade colloidal gold particles have become popular as markers in cytochemistry applications. Colloidal gold particles may be prepared in a variety of sizes through the reduction of gold chloride, or similar compounds, with a variety of reagents, including white phosphorus, sodium ascorbate, or sodium citrate. Colloidal gold particles generally have an average diameter of from 1 to about 140 nm.

Colloidal gold particles are typically bound to proteins or immunoglobulins to form protein-colloidal gold complexes, these protein-colloidal gold complexes are useful for the visualization of immunoreactions. For example, protein-colloidal gold complexes are widely used as electron-dense markers for electron microscopy, as colored markers in light microscopy, as stains for identifying substances on blots, and as a visible indicator for the presence of various substances in solution, such as hormones in urine.

The adsorption of proteins onto the colloidal gold is variable, depending to a great extent on the reaction conditions. Reaction conditions which have been identified as being most important include the amount of colloidal gold, the concentration of protein, and the pH of the reaction solution.

It is desirable that protein-colloidal gold complexes have a uniform size, shape, charge, and ratio of charge to size. In other words, the complexes are preferably homogeneous. Homogeneity is an important factor in predicting the reactivity of complexes, and further the reproducibility of experimental results obtained using them. The term "homogeneous" or "homogeneity" as used herein is defined as relating to a product producing substantially symmetrical spots after subjection to electrophoretic migration on a flat bed gel electrophoresis system. Electrophoretically homogeneous protein-colloidal gold complexes, or a discrete fraction thereof, are defined in greater detail as occupying a discrete area in the gel, immediately following electrophoresis, which is (at least with one dimensional electrophoresis) no greater than the diameter of the round sample well plus about 10% (perpendicular to the electrophoretic migration path); such areas are preferably round, or one axis of the area may be slightly elongated but no more than about 1.34 times the diameter of the sample well (about 33% increase, parallel to the electrophoretic migration path). One aspect of homogeneity is related to the quantity of protein bound by the gold particles. It is known that the amount of protein attached to the colloidal gold likely influences any experimental results obtained. Therefore, a homogeneous preparation would be superior to one that is either unknown or known to be non-homogeneous.

The testing and selection of homogeneous colloidal gold-protein complexes has in the past been largely restricted to only a few procedures including absorbance (1-3); passive gold agglutination (3); blotting (4-7); and centrifugation combined with direct observation in the electron microscope (8,9). The most commonly used methods for determining the homogeneity and usefulness of a particular preparation involves either a visual or spectrophotometric determination of the color change that occur when NaCl is added to the mixture. The spectrophotometer is used to determine the smallest absorbance or color change produced following the addition of NaCl to the protein-colloidal gold solution. These procedures are used not only to identify homogeneous preparation but also to select the pH and protein concentration that yield the lowest absorbance. Proponents of this method contend that solutions having a low absorbance contain minimal aggregates of complexes, and are therefore, homogeneous.

Visual and spectrophotometric methods essentially only distinguish between non-aggregated and aggregated preparations and do not identify the more subtle differences in the complexes which create heterogeneity. For example, more than one set of reaction conditions may be used to produce protein-colloidal gold complexes, which, according to spectrophotometric comparison, have identical or near identical absorbance, or degree of aggregation. However, it has been determined that the reactivity of these complexes is often different. Accordingly, visual or spectrophotometric methods cannot determine the homogeneity of a preparation. In addition, although direct observation with an electron microscope, centrifugation or chromatography can be used to identify, and in some cases even remove aggregates from a solution, unfortunately, however, these procedures do not detect more subtle differences between the particles themselves.

In light of the above deficiencies in the art, and the need for homogenous preparations of protein-colloidal gold complexes, it would be advantageous to provide a method for identifying the reaction conditions which produce homogeneous protein-colloidal gold complexes. Further, it would be advantageous to provide a method for producing homogeneous protein-colloidal gold complexes. Still further, it would be an advantage to provide a homogeneous protein-colloidal gold preparation. The present inventor has discovered that the electrophoretic mobility of protein-colloidal gold complexes can be used in the identification and production of homogeneous preparations. More particularly, it has been determined that complexes which exhibit an electrophoretic mobility which closely resembles that exhibited by the unbound free protein, are homogeneous.

SUMMARY OF THE INVENTION

One aspect of the present invention is directed to a method for producing homogeneous protein-colloidal gold complexes. According to the method, a sample of protein-colloidal gold complexes is subjected to electrophoretic separation. A fraction of the sample which migrates during electrophoresis as a discrete fraction is then identified. Thereafter, the identified fraction is removed from the electrophoretic medium. The removed fraction consists of homogeneous protein-colloidal gold complexes as determined through either one or two-dimensional electrophoresis.

In accordance with a preferred embodiment, the protein is selected from the group consisting of monomeric Bovine Serum Albumin (BSA) dimeric BSA, monomeric Human Serum Albumin (HSA), and dimeric HSA. Since the complexes of the instant invention are useful in immunochemical applications, according to a further preferred embodiment, the protein is an antigen or an antibody.

A further aspect of the present invention is also directed to a method for producing homogeneous protein-colloidal gold complexes. In accordance with the invention, the method provides that a selected quantity of homogeneous colloidal gold particles and a predetermined concentration of a homogeneous protein are reacted at a particular pH to form a suspension of protein-colloidal gold complexes. This step is preferably repeated several times, wherein each repetition is performed with at least one of a different pH, a different concentration of the protein, or a different amount of the colloidal gold. A fraction from each suspension of protein-colloidal gold complexes so produced is electrophoresed. Thereafter, a fraction which migrates through the electrophoretic medium as a discrete fraction is identified. The identified fraction consists essentially of homogeneous protein-colloidal gold complexes. In accordance with one preferred embodiment, the reaction conditions under which the homogeneous fraction was produced are reproduced to manufacture a quantity of homogeneous complexes. Preferred reaction conditions include a concentration of protein from about 75 to about 250 micrograms/ml and a pH of from about 5.0 to about 7.0.

A still further aspect of the present invention is directed to a composition of protein-colloidal gold complexes, wherein the composition migrates through an electrophoretic medium as a discrete unit. It has been determined that such migration is indicative of homogeneity.

BRIEF DESCRIPTION OF THE DRAWINGS

FIG. 1 shows the chromatographic separation of monomeric and dimeric BSA ($BSA_M$ and $BSA_D$ respectively) by molecular weight on Sephadex G150. Panel A shows the chromatographic separation peak for the BSA monomer. Panel B shows the chromatographic separation peak for the BSA dimer.

FIG. 3 panel A shows the coagulation curves for the adsorption of $BSA_M$ to colloidal gold at a pH from 5.5 to 9.0; panel B shows the coagulation curve for the adsorption of $BSA_D$ to colloidal gold at a pH of from 5.5 to 7.0.

DESCRIPTION OF THE PREFERRED EMBODIMENTS

One aspect of the present invention is the preparation of homogeneous protein colloidal gold complexes. Variability in the complexes results from the adsorption of different quantities of protein onto the gold particle (10,11). It has herein been demonstrated that this phenomena is caused by the pH of the reaction solution, and the concentration of protein or colloidal gold present. Presently, no method is available which accurately identifies the homogeneity or the heterogeneity of a particular sample of protein-colloidal gold complexes.

Figure 5:
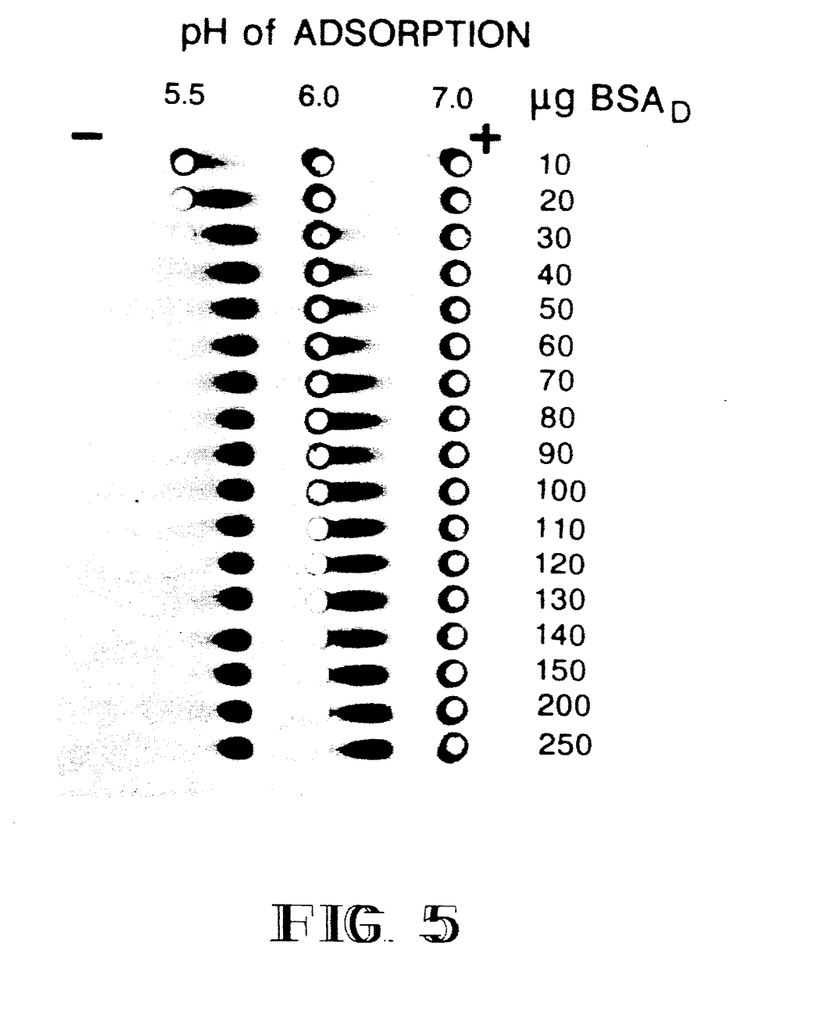
FIG. 5 is a photograph of the one-dimensional particle gel electrophoresis in 1% Aldrich agarose of $BSA_D$-colloidal gold at various protein concentrations and pH values.
Figure 7:
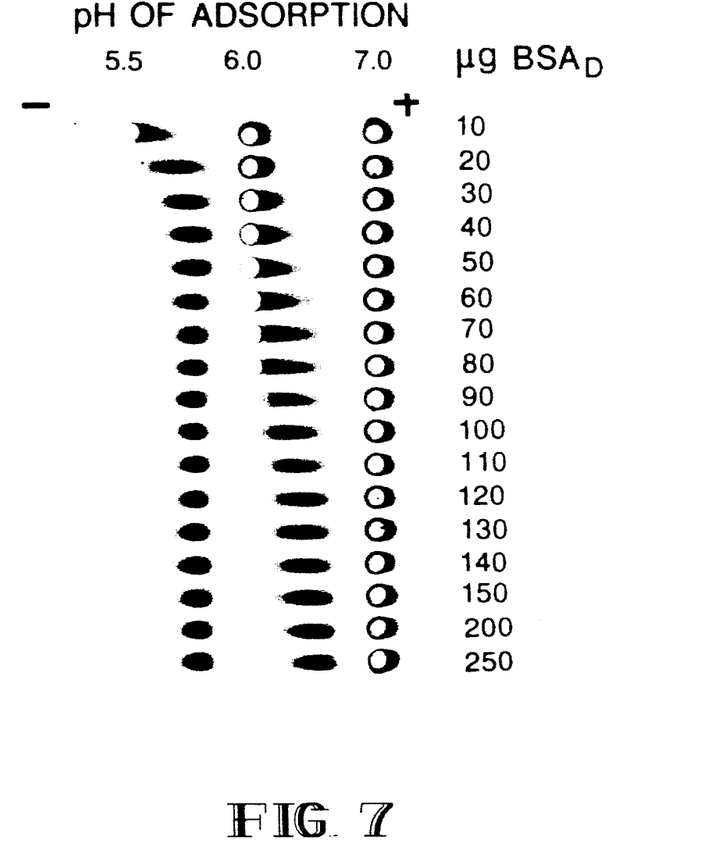
FIG. 7 is a photograph of the one-dimensional particle gel electrophoresis of $BSA_D$-colloidal gold in 1% IsoGel at various protein concentrations and pH values.
Figure 8:
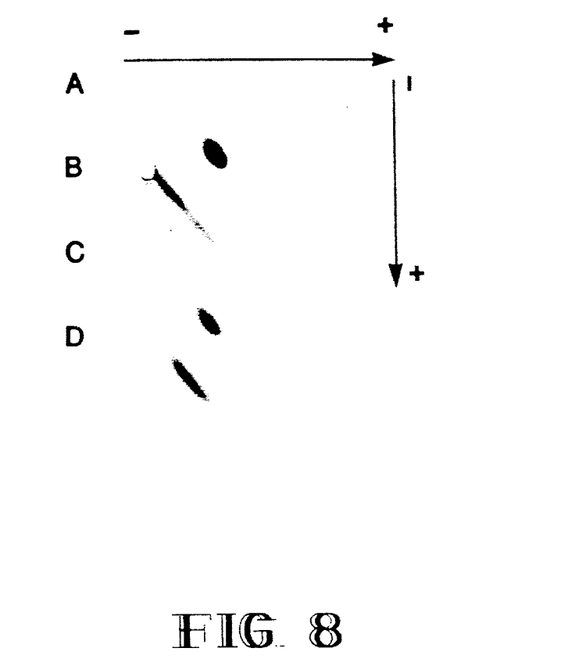
FIG. 8 is a photograph of the two-dimensional particle gel electrophoresis in 1% IsoGel at various protein concentrations and pH values. A is 160 μg $BSA_D$ adsorbed to colloidal gold at pH 5.5; B is 70 μg $BSA_D$ adsorbed to colloidal gold at pH 6.0; C is 170 μg $BSA_M$ adsorbed to colloidal gold at pH 5.5; and D is 100 μg $BSA_M$ adsorbed to colloidal gold at pH 6.0. The top arrow indicates the direction of electrophoresis for the first hour and the arrow pointing in the down direction indicates the direction of electrophoresis for the second hour.

In accordance with one aspect of the invention a sample of protein-colloidal gold complexes is subjected to electrophoretic separation. One or two dimensional particle gel electrophoreses are the preferred electrophoresis procedures. A fraction of the sample which migrates during electrophoresis as a discrete fraction is thereafter identified. The term "discrete fraction" is intended to mean a fraction which appears to migrate as spot or band through the electrophoretic medium without blurring or trailing material throughout the medium. An example of a "discrete fraction" migrating through an electrophoretic medium in one-dimensional electrophoresis is seen in FIGS. 5, and 7 as the fractions produced in a pH of 5.5 solution and a protein concentration of 250 micrograms/ml. An example of a discrete fraction migrating through an electrophoretic medium during two-dimensional electrophoresis is shown in FIG. 8 as the spots identified as "A" and "C". One type of electrophoretic medium useful in the practice of the present invention is agarose gel.

Complexes which migrate together through an electrophoretic medium are homogeneous. The electrophoretic migration of a particle in agarose is determined by the surface net charge density and by retardation of the particle migration according to size. Therefore, complexes which form a migrating discrete fraction not only are the same size but also have the same surface net charge. This can be interpreted as demonstrating that the colloidal particles must have identical amounts of protein bound to their surfaces, and are accordingly, homogeneous.

Once a migrating spot is identified as a discrete fraction, it is removed from the electrophoretic medium. The fraction consists of homogeneous protein-colloidal gold complexes. These complexes are preferably washed and used in research or medicine. Homogeneous complexes would be especially useful in these areas if their reactivity was predictable and the results obtained, reproducible. Results obtained with these complexes should have all of these qualities since the complexes of the present invention are homogeneous and will react predictably, and will reliably provide reproducible results.

Protein useful in the practice of the invention includes proteins which are antigens or antibodies. This is particularly preferred since protein-colloidal gold complexes are used frequently in cytochemical and immunochemical applications. Preferred protein include monomeric BSA, dimeric BSA, monomeric HSA, and dimeric HSA. However, it should be realized that all proteins which bind to colloidal gold particles are potentially useful in the practice of the present invention.

In accordance with another aspect of the present invention, a further method for producing homogeneous protein-colloidal gold complexes is provided. According to this method, a selected quantity of homogeneous colloidal gold particles is reacted with a predetermined concentration of a homogeneous protein at a particular pH to form a suspension of protein-colloidal gold complexes.

The colloidal gold particles preferably have a diameter of from about 1 to about 140 nm. More preferably, depending upon a particular use, the colloidal gold particles have a diameter of from about 5 to 10 nm, 15 to 20, and most preferably from about 1 to about 5 nm. It should be noted that the diameter of the gold particles is important only to the specific application. For example, certain immunochemical applications preferably involve particles having the smallest possible diameter, while in other applications diameter is irrelevant. Although the diameter of the gold particles may be important, it is also important that the colloidal gold particles are homogeneous. In one example below, the homogeneous colloidal gold particle used have a diameter of from 18 to 20 nm. Homogeneous gold particles are available commercially or may be manufactured using techniques well known in the art.

The proteins useful in the practice of the present invention are also preferably homogeneous. Although commercially available protein preparations often claim to be homogeneous, it is demonstrated herein that some of these preparations generally are not homogeneous and should be purified before use.

According to the inventive method several different concentrations of protein are reacted with several different amounts of colloidal gold in solutions having several different pH values. This is preferable so that the conditions under which homogeneous complexes are produced be investigated and identified. Once these conditions are identified the protein and the colloidal gold particles can be reacted repeatedly under substantially the same reaction conditions which were used to produce the initial homogenous sample to produce further quantities of homogeneous protein-colloidal gold complexes.

Preferably, the reaction solution has a pH of from about 5.0 to about 7.0, and more preferably, from about 5.5 to 6.0. The concentration of the protein in the reaction solution is preferably from about 10 to about 500 micrograms/ml. More preferably, the concentration of the protein is from about 75 to about 250 micrograms/ml, and most preferably about 250 micrograms/ml. It should be noted, however, that the most preferred concentration of protein and the most preferred reaction solution pH will vary, depending on which protein is selected.

A fraction from each suspension of protein-colloidal gold complexes produced as described above is thereafter electrophoresed. Subsequently, a fraction which migrates through the electrophoretic medium as a discrete fraction is identified. As discussed above the identified fraction consists essentially of homogeneous protein-colloidal gold complexes.

The present invention is particularly advantageous when it is considered that past procedures were not able to distinguish between homogeneous and heterogenous preparations. For example, procedures which essentially relied upon color change, whether based upon visual assessment (12), spectrophotometric measurements (13), are inherently unable to determine homogeneity in various preparations. The use of electrophoresis to produce homogeneous complexes and to identify the conditions for the homogeneous adsorption of protein to colloidal gold appears to represent a significant and advantageous departure from past procedures.

The following examples are included to more fully describe the present invention, to present currently preferred embodiments and to insure that the present description enables one skilled in the art to practice the present invention. These examples are not intended to limit the scope of the present invention beyond that otherwise specific in the claims appended hereto.

EXAMPLES

Materials and Methods

Proteins: $BSA_M$ was obtained as lyophilized powder A-1900 and $BSA_D$ was obtained as lyophilized powder A-9039, from the Sigma Chemical Co., St. Louis, Mo.

Preparation of BSA for Adsorption: $BSA_M$ was purified further as described previously by Habeeb (14). Briefly, 500 mg of $BSA_M$ were dissolved in 0.005M sodium phosphate buffer pH 6.2 and chromatographed on a DEAE cellulose column (DE 52 Whatman, Clifton, N.J.) equilibrated with the same buffer. The column was eluted stepwise using 0.0175M sodium phosphate buffer pH 6.2; 0.0175M sodium phosphate buffer plus 0.075M NaCl pH 6.2; 0.175M sodium phosphate buffer plus 0.2M NaCl pH 6.3; and finally with 0.0175M sodium phosphate buffer plus 0.5M NaCl pH 6.2. Following elution from the DE 52 column, with 0.175M sodium phosphate buffer with 0.2M NaCl pH 6.2, the major BSA peak (peak 3) was rechromatographed on Sephadex G150 (Pharmacia, Piscataway, N.J.) to remove BSA polymers (15) which form during lyophilization. No attempt to fractionate $BSA_D$ by ion exchange was made and the $BSA_D$ population utilized may be heterogenous with respect to the character of the BSA molecule in each dimer (14). $BSA_D$ were chromatographed on G150 to eliminate monomers and non-dimeric polymers. The proteins were sterile filtered and stored on 0.01M sodium phosphate buffer containing 0.9% NaCl pH 7.3 (PBS) at 4° C.

Desalting BSA: Prior to adsorption of BSA, 2 ml of fractionated BSA was added to the top of a prepacked disposable PD-10 column containing Sephadex G-25M (Pharmacia) which had been washed extensively with water to remove the preservative. Fractions, 0.9–1.0 ml, were collected and the protein peak determined at 280 nm. The position of the buffer was determined by measuring pH. Typically, the last tube containing a small quantity of protein also contained enough buffer to shift the pH towards the pH of the buffer; this fraction was not used. The remaining BSA fractions were combined and the BSA concentration adjusted to 1 mg/ml based on the absorbance of BSA at 279 nm.

Colloidal Gold: Colloidal gold was produced from $HAuCl_4 \cdot 3H_2O$ obtained from the Aldrich Chem. Co., Milwaukee, Wis., by reducing it with sodium citrate. A single homogeneous batch of colloidal gold having a diameter of 18–20 nm was used in all investigations. As a result, the surface area for adsorption was identical in each sample. The pH was adjusted in the alkaline direction by the addition of 0.01, 0.1 or 0.2M $K_2CO_3$ or in the acidic direction by the addition of 0.5 or 0.05N acetic acid. The pH was determined using a gel-filled electrode from Markson, Phoenix, Ariz. The colloidal gold used in these experiments had an absorbance of 0.90 at 525 nm. The spectrophotometer was zeroed with $H_2O$.

Adsorption: Coagulation curves were constructed as described below. Briefly, protein in 1 ml volumes was added to 5 ml of vortexing colloidal gold, pH adjusted, at 22° C. After 1 minute 1 ml of 10% NaCl was added to the vortexing mixture. After 5 minutes, the absorbance of each sample was determined using a Gilford spectrophotometer from Gilford, Oberlin, Ohio, with a 1-cm light path, which had been zeroed at 580 nm with a blank consisting of 5 ml of the colloidal gold plus 2 ml of $H_2O$. The difference in absorbance was graphed.

Sample Preparation for Particle Electrophoresis: In addition to the samples prepared for determination of the coagulation curves, duplicate samples were prepared from the same protein and colloidal gold solutions in the same manner except that 1 ml of 0.1% polyethylene glycol 20M obtained from the Fisher Chemical Co., Houston, Tex., instead of NaCl, was added to each sample 1 minute after the addition of protein to avoid the coagulating effects of the NaCl and to stabilize colloidal gold which had not been stabilized by the BSA.

Prior to electrophoresis, the pH of BSA-colloidal gold prepared at pH 5.5 and 6.0 was adjusted to pH 7.0–8.0 with dilute $K_2CO_3$. Adjusting the pH to a more alkaline value eliminated losses during centrifugation caused by aggregation of some BSA-colloidal gold preparations on the bottom wall of the centrifuge tubes. 1 ml from each sample was centrifuged at 20,000 rpm for 20 minutes at 16° C. in a TL 100.2 rotor using a Beckman TL 100 centrifuge. The rotor was permitted to coast to a stop. Following centrifugation, 900 µl of supernate was removed gently with an adjustable 1000 µl pipet (Pipetman, Rannin, Woburn, Msdd.) leaving a small liquid red droplet at the bottom of each tube in 100 µ of supernate. If discoloration or caking of the BSA-colloidal gold complex was noted, following centrifugation, the pH of the remaining 4 ml of that BSA-colloidal gold sample was made more alkaline with $K_2CO_3$, e.g., adjusted one pH unit, and a second 1 ml sample was centrifuged. The red BSA-colloidal gold droplet was gently shaken to resuspend the BSA-colloidal gold in the remaining supernate and each sample was transferred to a small polypropylene test tube and capped to prevent evaporation.

One Dimensional Particle Electrophoresis in 1% Agarose: Agarose, 2.0 g, having an EEO value of 0.13 was obtained from the Aldrich Chemical Co., Milwaukee, Wis. and agarose, IsoGel, having an EEO value of approximately 0.0 was obtained from the FMC BioProducts, Rockland, Me. The agarose was dissolved by heating in a microwave oven, in 200 ml of 0.02M tris, 0.006M tricine (Research Organics, Cleveland Ohio), and 0.027 g calcium lactate $5H_2O$/ liter (Fluka AG, Switzerland) pH 8.6. This buffer was modified from that originally described by Monthony et al. (16) by decreasing the concentrations of each of the components by 75%. Barbital buffers may also be used, however, barbital buffers crystallize extensively on drying which makes comparison of each sample more difficult. By contrast, the tris-tricine buffer produces a relatively transparent film such that the gels may be examined after drying (16). The hot liquid agarose, 10 ml, was pipetted onto an 8.3×10.2 cm Kodak projector slide cover glass which had been cleaned with Micro (International Products, Trenton, N.J.). GelBond (FMC BioProducts) may be used in place of glass slides. The agarose coated slides were stored in a moist chamber for a minimum of 1 hour after pouring the gel. wells, 3 mm in diameter, were punched in the gel using a BioRad Universal puncher and multiwell punching template (BioRad, Richmond, Calif.). Each gel was connected using paper wicks (cut from Whatman No. 1 filter paper sheets) to anode and cathode buffer chambers containing the same buffer used to prepare the gel. BSA-colloidal gold, 6 µl, was added to each well and the gels were electrophoresed using an LKB 2197 power supply set for 200 volts constant, 10 mA and 5 watts limiting for 1 hour. The current and power were allowed to adjust automatically but typically ran at 200 volts, 1–4 mA depending on the buffer used and 1–2 watts. At the end of the one hour time period the power supply shut itself off automatically.

Upon completion of each electrophoretic run the non-gel side of the glass plate was wiped dry and the gel dried overnight in a 60° C. oven. When the gels were dried at 60° C. they were clear, hard and free of any buffer precipitates although after long term storage some buffer precipitates occasionally formed. The salts were easily removed by dipping the glass slide briefly into distilled water until the salts dissolved.

Two Dimensional Particle Electrophoresis: This electrophoretic procedure was identical to that described for one dimensional particle electrophoresis except that after an initial one hour period of electrophoresis the glass plate was rotated 90° followed by electrophoresis for an additional one hour period. The wicks were removed before the glass plate was rotated 90°. Then the wicks were reattached.

Electrophoresis of BSA: $BSA_D$ and $BSA_M$ were electrophoresed in both 1% Aldrich and 1% IsoGel agarose using the same buffer utilized in particle electrophoresis. Gels were poured on clean 3 inch by 1 inch microscope slides, 3 ml of agarose per slide, and used after storing in a moist chamber for a minimum of one hour. Gels were connected to buffer tanks using Whatman Chromatography paper set at a medium flow rate, and the proteins were electrophoresed at 200 volts constant, 10 mA and 5 W limiting for one hour at room temperature. The slides were fixed and stained with coomassie blue as described for isoelectric focusing.

Isoelectric Focusing: The isoelectric points (pI) of BSA were determined by isoelectrofocusing in IsoGel agarose IEF plates pH 3–10 according to the manufacturers instructions (FMC BioProducts, Rockland Me).

BSA for isoelectrofocusing was concentrated by centrifugation in a Centricon-10 Amicon, Danvers, MA with a membrane having a 10,000 molecular weight cutoff. The salts were removed by the addition of distilled water and recentrifuging the sample. 2.5 $\mu$l samples of BSA, containing approximately 2.5 $\mu$g BSA, were pipetted into the slots on an application mask on the gel and were electrophoresed into the gel at 1 W constant power for 10 minutes. After removal of the mask the gel was electrophoresed for an additional 30 minutes at 1500 volts limiting (LKB 2197 power supply). Fixation and staining were performed by a modification of LKB procedure 1818-A. The pI range of each protein was determined by comparison to focused pI markers (Pharmacia; Piscataway, N.J.).

Passive Gold Agglutination (PGA): PGA was performed to determine the reactivity of different BSA-colloidal gold preparations with rabbit anti-BSA serum (Sigma B-150), 1 ml samples of colloidal gold were centrifuged at 20,000 rpm for 20 minutes at 16° C., resuspended in 0.1% polyethylene glycol (PEG) pH 9.0 and centrifuged again under the same conditions. The samples were centrifuged three times to remove unbound BSA. Each sample was resuspended to the original volume in 0.01M sodium phosphate buffer pH 7.3 containing 0.9% NaCl and 1% PEG. PGA was performed as previously described except that the absorbance of the samples was not readjusted to 0.6 at 525 nm and the microtiter plates were centrifuged at 3000 rpm for 10 minutes at room temperature.

Figure 1A:
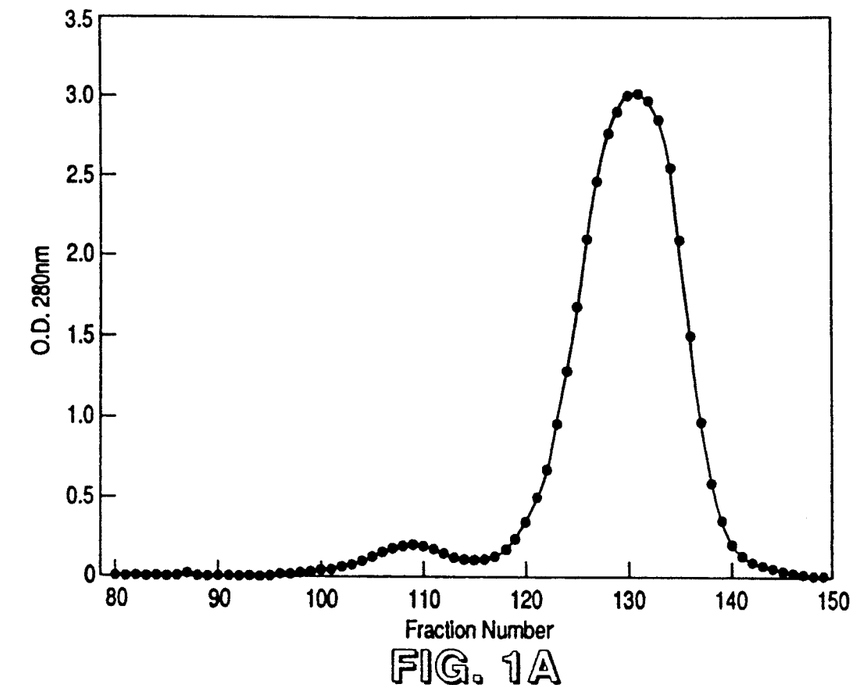
Figure 1B:
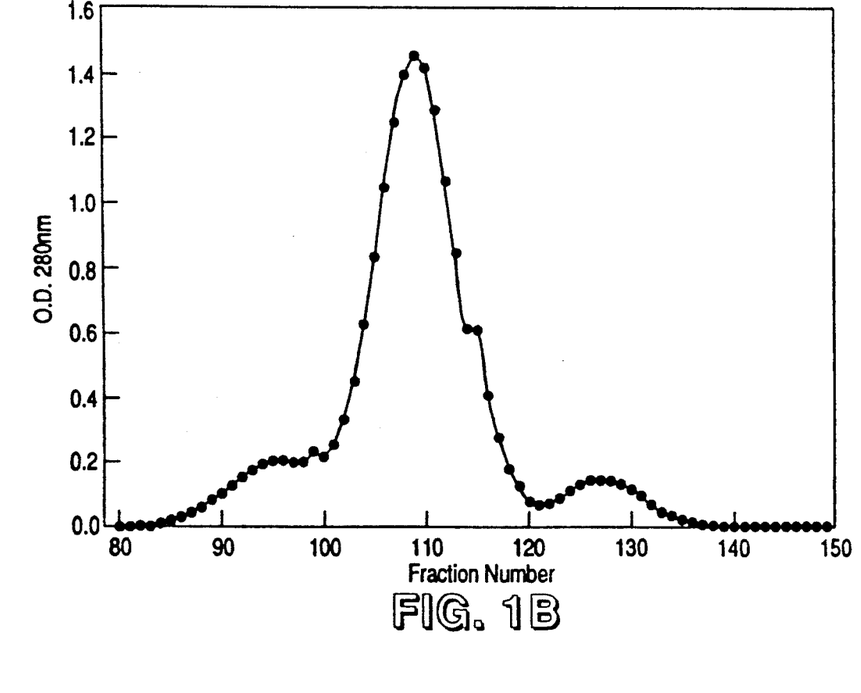

The pI values of BSA purified by ion exchange and/or gel permeation chromatography were determined to be $BSA_M$ 4.57–4.78 and $BSA_D$ 4.55–5.18. Both preparations of BSA were supplied as lyophilized powders and each sample contained primarily the monomer or the dimer, as indicated by the manufacturer. The results in FIG. 1 demonstrate that both commercial protein preparations were contaminated by monomeric and/or polymeric BSA. The monomeric or dimeric fractions were carefully selected from their respective peaks, sterile filtered and stored in PBS at 4° C. They were maintained in solution to avoid induction of polymer formation.

Figure 2:
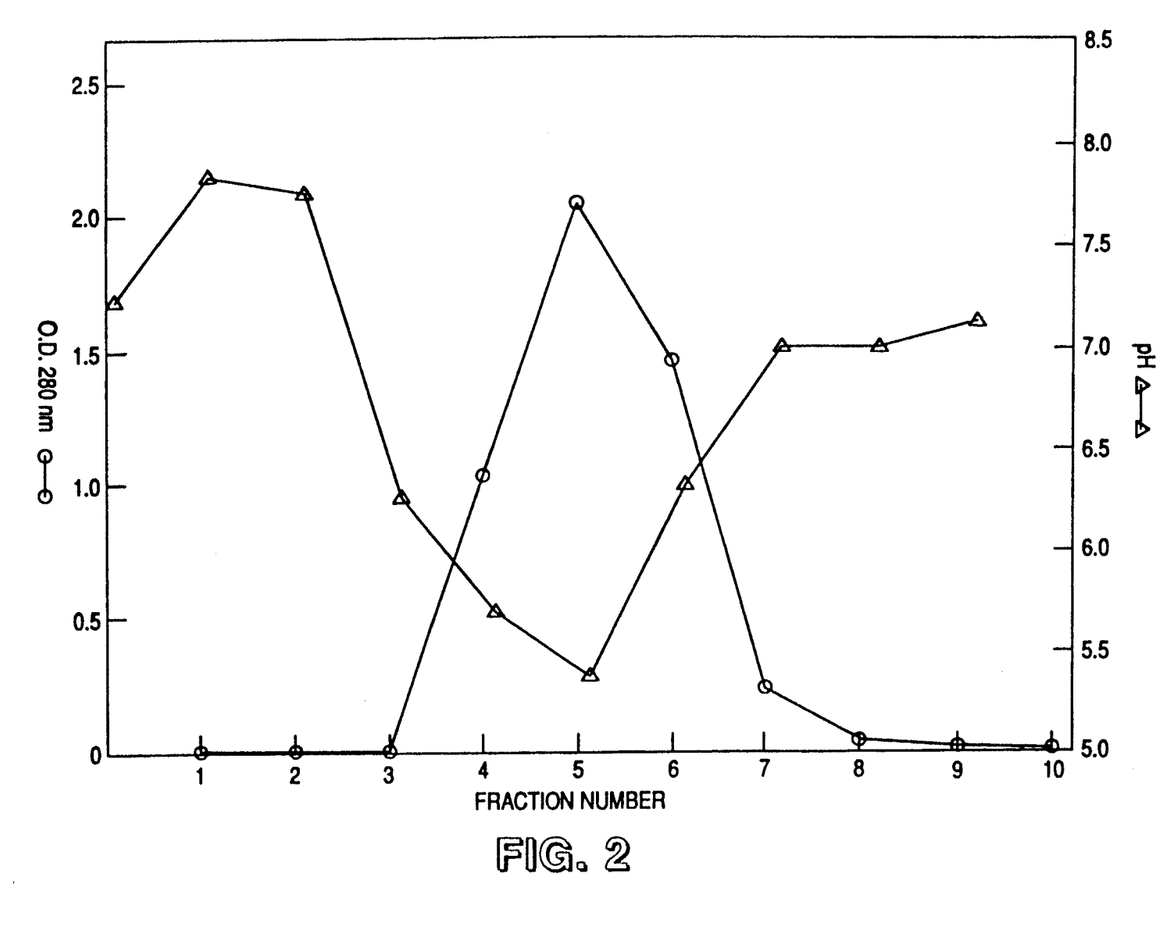
FIG. 2 shows the chromatographic separation of BSA from buffer salts on a PD10 column.

The graph in FIG. 2 was typical of the separations of BSA from buffer salts obtained when 2 ml of BSA in 0.01M sodium phosphate buffer containing 0.9% NaCl pH 7.3 was passed through a PD10 column previously equilibrated with distilled water. The BSA had been sterile filtered and stored at 4° C. in 0.01M sodium phosphate buffer containing 0.9% NaCl pH 7.3. Following the brief chromatographic separation the presence of the buffer was easily detected by a shift in the pH of the eluent. BSA was detected by determining the absorbance of each fraction at 280 nm. The measured pH of the eluent decreased as the BSA eluted and then increased as the buffer salts eluted from the column. Fraction numbers 4, 5 and 6 were combined in this instance and the BSA concentration adjusted to 1 mg/ml using the molar extinction coefficient of BSA to calculate the protein concentration.

Proteins desalted by passage through a PD10 column were added to the colloidal gold without causing a large shift in the pH of the colloidal gold. For example BSA desalted on a PD10 column, when added to 5 ml of pH 8.0 colloidal gold, caused the pH to shift only 0.02–0.06 pH units. This represented a pH shift similar to that caused by the addition of an equal volume of distilled water. Desalting required much less time than dialysis, i.e., 24–48 hours, and chance bacterial contamination of the protein was subsequently reduced.

Figure 3A:
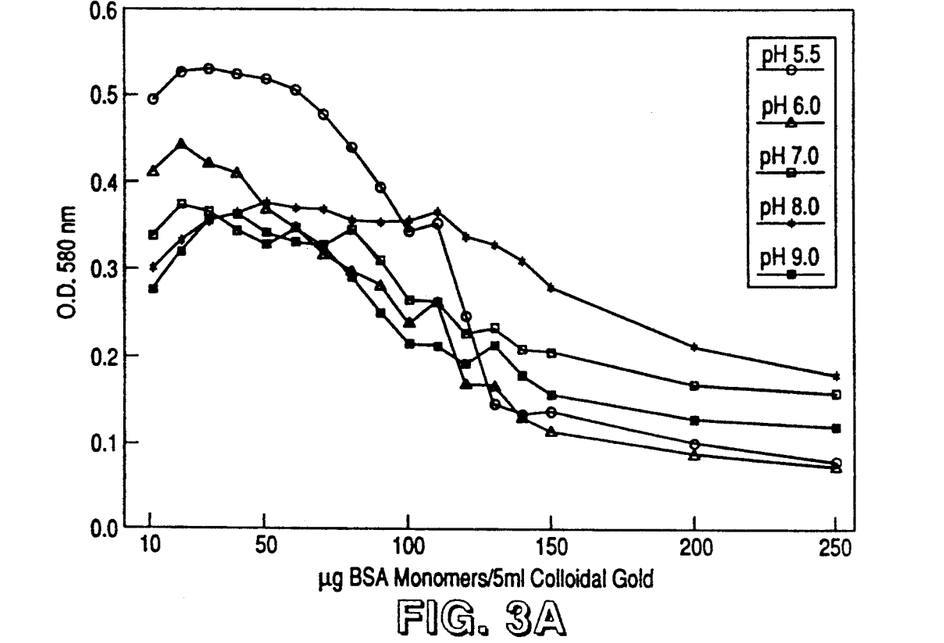
Figure 3B:
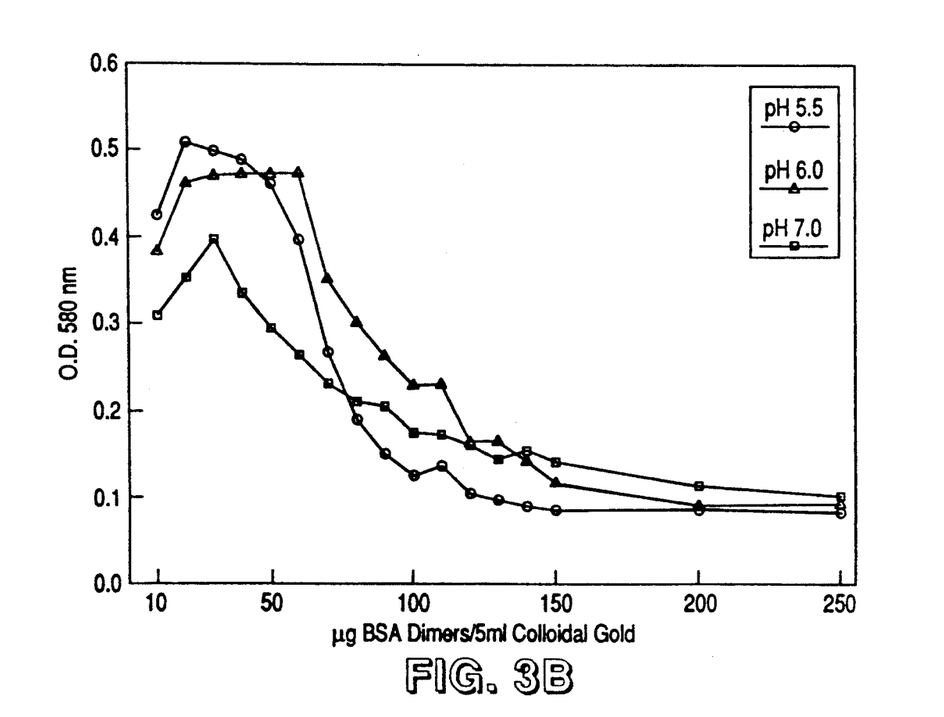

It has been the general practice that the pH of adsorption and the quantity of protein reaction with the colloidal gold was based on the combination of the two variables yielding the lowest absorbance. Further, it was believed that preparations having a low absorbance contained no aggregates and was homogenous. In FIG. 3, similar absorbencies were obtained for the adsorption of BSA at 200–250 $\mu$g BSA/5 ml colloidal at pH 5.5 and pH 6.0. Because the absorbencies were similar, one might readily select either pH 5.5 or pH 6 for the adsorption of $BSA_D$ or $BSA_M$ in the production of homogenous preparations. In addition to difficulties in selecting the better pH of adsorption, the selection of one BSA concentration over another also presented a problem. No clear endpoint in the absorbencies were apparent, the absorbance continued to decrease with each increase in the quantity of $BSA_M$ added. Further, the variability in absorbance values was also a problem for the adsorption of $BSA_D$ at pH 6.0 and pH 7.0. However, nearly identical absorbance values were obtained for the adsorption of 150 to 250 $\mu$g $BSA_D$ at pH 5.5. Samples of $BSA_M$-colloidal gold prepared at some pH values, i.e., pH 7, 8 or 9, were readily distinguished by greater absorbencies suggesting that the colloidal gold had not been homogenized, or stabilized as well at these pH values.

Figure 4:
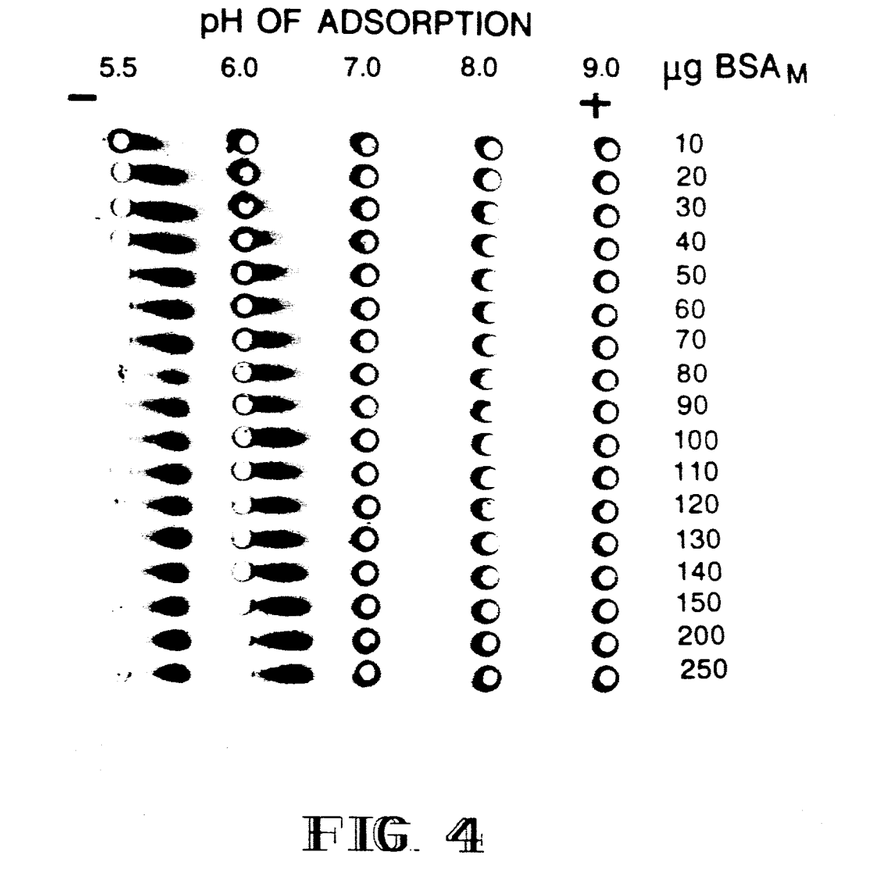
FIG. 4 is a photograph of the one-dimensional particle gel electrophoresis in 1% Aldrich agarose of $BSA_M$-colloidal gold at various protein concentrations and pH values.

To compare the effects of varying the pH of adsorption and the BSA concentration on the homogeneity of the preparation as measured by electrophoretic mobility of the resulting BSA-colloidal gold complexes, samples were prepared as described for the coagulation curves except that 1 ml of 0.1% PEG was substituted for 1 ml of 10% NaCl. The purpose of substituting the PEG for the NaCl was to avoid coagulating any of the product. In addition, PEG-colloidal gold has been shown to migrate towards the cathode in agarose while BSA migrates towards the anode. FIGS. 4 and 5 show that the electrophoresis of each of the resulting samples in 1% Aldrich agarose revealed major differences in the electrophoretic mobilities of BSA-colloidal gold prepared at the various pH values and protein concentrations.

$BSA_M$-colloidal gold (pH 5.5) migrated towards the anode regardless of the quantity of protein added. However, a small quantity remained in the wells and did not migrate at the lowest protein concentrations. The shape of the electrophoretic pattern changed markedly as the quantity of protein added increased. The electrophoretic pattern was shortest at 10 $\mu$g $BSA_M$. As the quantity of added $BSA_M$-colloidal gold (pH 5.5) increased the length of the pattern increased. At 30 $\mu$g $BSA_M$, the distance of migration appeared to stabilize with respect to the length from the well to the leading edge of the $BSA_M$-colloidal gold (pH 5.5). As the quantity of protein added was increased further, the electrophoretic pattern of the densest portion of the $BSA_M$-colloidal gold appeared to become more compact while the quantity of $BSA_M$-colloidal gold trailing the more compact and electrophoretically faster portion of $BSA_M$-colloidal gold appeared to grow fainter until it appeared to lose its connection to the well. In fact, only a very small connection, not clearly visible in the FIGS., was present at 250 $\mu$ $BSA_M$.

The electrophoretic pattern of the $BSA_M$-colloidal gold (pH 6.0) remained elongated regardless of the quantity of $BSA_M$ added. Even at 250 $\mu$g $BSA_M$, the pattern remained elongated although the segment closest to the well appeared to become less dense and finally to almost lose contact with the well at 250 μg BSA$_M$.

BSA$_M$-colloidal gold prepared by adsorption of BSA$_M$ to colloidal gold at pH 7, 8 or 9 did not migrate towards the anode, although a portion of the complex remained in each well which upon drying left a fine red ring on the anodal side of the wells. Most of the BSA$_M$-colloidal gold prepared at pH 7, 8 or 9 migrated to the cathodal side of each well and into the gel.

FIG. 5 shows the electrophoresis of the BSA$_D$-colloidal gold in 1% Aldrich agarose yielded results similar to those observed for BSA$_M$-colloidal gold. As shown in FIG. 5, BSA$_D$ was not adsorbed at pH 8 or 9. Samples prepared at pH 5.5, pH 6 and pH 7 resulted in BSA$_D$-colloidal gold mobilities which were similar to those observed for BSA$_M$-colloidal gold prepared at the same pH values and protein concentrations. The length of the electrophoretic pattern of BSA$_D$-colloidal gold (pH 5.5) decreased from 9 mm at 30 μg BSA$_D$ to 8 mm at 120 μg BSA$_D$ but more impressively the trailing or more slowly moving portion of the BSA$_D$-colloidal gold (pH 5.5) seemed to almost disappear while the dense area appeared to represent nearly all of the sample. BSA$_D$-colloidal gold (pH 6.0) like BSA$_M$-colloidal gold (pH 6.0) exhibited a more elongated pattern than the BSA$_D$-colloidal gold (pH 5.5) although as the quantity of BSA$_D$ added increased to 250 μg a shorter and more compact migration pattern began to appear. BSA$_D$-colloidal gold (pH 7.0) migrated towards the cathode as described for BSA$_M$-colloidal gold (pH 7.5 and 90).

Figure 6:
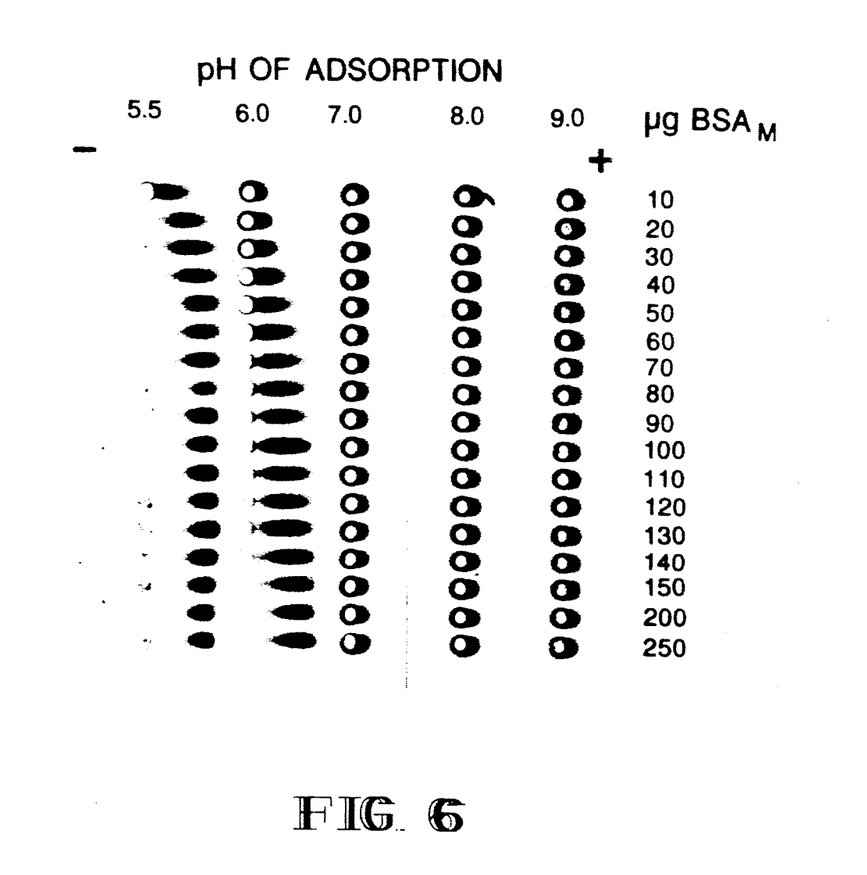
FIG. 6 is a photograph of the one-dimensional particle gel electrophoresis of $BSA_M$-colloidal gold in 1% IsoGel at various protein concentrations and pH values.

Aldrich agarose has an electroendosmotic value of 0.13 according to the manufacturer. To eliminate electroendosmotic effects on the migration patterns 1% IsoGel agarose was substituted for the 1% Aldrich agarose as shown in FIGS. 6 and 7. The charges on the agarose used in IsoGel are largely neutralized due to the addition of clarified locust bean gum by the manufacturer. Two general comparative observations are made between electrophoresis in Aldrich agarose versus IsoGel: 1) the eleotrophoretic patterns in IsoGel appeared sharper or less fuzzy than those in the Aldrich agarose, and 2) the BSA$_D$-colloidal gold and BSA$_M$-colloidal gold complexes migrated a greater distance in 1% IsoGel than in 1% Aldrich agarose, e.g, a sample of BSA$_M$-colloidal gold (pH 5.5) that migrated 12.5 mm in 1% IsoGel migrated 10 mm in 1% Aldrich agarose.

As shown in FIG. 6, the migration of BSA$_M$-colloidal gold (pH 5.5) in 1% IsoGel varied as the quantity of BSA$_M$ added increased. From 10-60 μg BSA$_M$ the pattern of BSA$_M$-colloidal gold (pH 5.5) changed from a short red stripe with a dense area nearest the well into a dense red oval area containing most of the complex followed by a reddish tail which became less dense as the quantity of BSA$_M$ added increased. As the BSA$_M$ concentration was increased the dense oval area shortened becoming more compact; this was especially noticeable between 20-110 μg BSA$_M$. At greater than 100 μg BSA$_M$ the electrophoretic changes were difficult to detect from one 10 μg increment to the next and appear to vanish at BSA$_M$ concentrations greater than 120 μ.

Also referring to FIG. 6, the migration of BSA$_M$-colloidal gold (pH 6.0) complexes also varied as the quantity of BSA$_M$ added was increased. From 10-70 μg BSA$_M$ the pattern increased in length. At 10 μg the pattern appeared as a dense nub on the anodal side of the well. As the quantity of BSA$_M$ added increased the dense area elongated but remained near the well while a faster but sparse population of BSA$_M$-colloidal gold (pH 6.0) advanced towards the anode and away from the well. At 80-120 μg BSA$_M$ the dense area expanded and the distance it migrated increased until it occupied the most anodal portion of the pattern. From 130-170 μg the dense area shortened but remained at the anodal from of the pattern and began to resemble the pattern of BSA$_M$-colloidal gold (pH 5.5) prepared using 40-50 μg BSA$_M$.

Referring to FIG. 7, BSA$_M$-colloidal gold also migrated farther in 1% IsoGel than in 1% Aldrich agarose. The length of the BSA$_D$-colloidal gold (pH 5.5) electrophoretic pattern decreased as the quantity of BSA$_D$ added increased from 20-150 μg. By comparison the length of the electrophoretic pattern of BSA$_D$-colloidal gold (pH 6.0) in 1% IsoGel increased as the quantity of BSA$_D$ added increased from 20-150 μg. The protein-colloidal gold complex resulting from the addition of BSA$_D$ at pH 7 migrated only a short distance towards the anode.

Passive gold agglutination was used to test the reactivity of the BSA-colloidal gold preparations produced at 250 μg BSA. It was found that only BSA adsorbed at either pH 5.5 or pH 6.0 could be agglutinated by rabbit anti-BSA serum. BSA adsorbed at pH 7-9 failed to be agglutinated by the rabbit antiserum.

The elongated electrophoretic patterns obtained for BSA-colloidal gold (pH 6.0) and for BSA-colloidal gold (pH 5.5) prepared at lower BSA concentrations suggested that these preparations were electrophoretically heterogeneous. To confirm this observation several samples were electrophoresed in two dimensions. The results presented in FIG. 8 were obtained first by electrophoresis in one direction. After one hour the gel was rotated 90° and electrophoresis was continued at 90° to the original direction for an additional hour. The results demonstrated that the relative positions of different parts of each electrophoretic pattern were maintained after the direction of migration was changed by 90°. The original elongated pattern, for BSA-colloidal gold prepared at pH 6, was retained except that it appeared to be moving at an angle of 45° to the original direction. A similar but shorter pattern for the BSA-colloidal gold prepared at pH 5.5 was retained.

Figure 9:
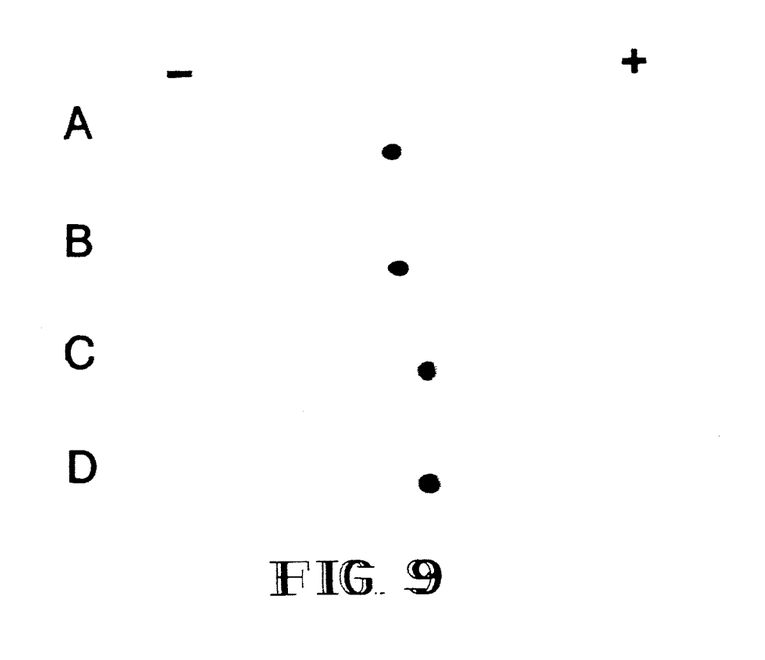
FIG. 9 is a photograph of the one-dimensional electrophoresis of $BSA_D$ and $BSA_M$. A is $BSA_D$ in 1% Aldrich agarose; B is $BSA_M$ in 1% Aldrich agarose; C is $BSA_D$ in 1% IsoGel; D is $BSA_M$ in 1% IsoGel.

Finally, referring to FIG. 9, for comparative purposes, unbound BSA$_D$ and unbound BSA$_M$ were electrophoresed in both 1% agarose and 1% IsoGel in the same buffer used for electrophoresis of the BSA-colloidal gold complexes. BSA migrated farther in IsoGel than it does in the Aldrich agarose. BSA exhibited an electrophoretic pattern which was round to oval or slightly tear shaped depending on whether it was electrophoresed in 1% Aldrich agarose (FIG. 9 Panel A and Panel B), or in IsoGel agarose (FIG. 9 Panel C and Panel D). These data suggest that the same or similar electrophoretic pattern would be desirable in BSA-colloidal gold preparations.

In the examples reported herein, coagulation curves as shown in FIG. 3, based on difference spectroscopy, were determined following the adsorption of variable quantities of BSA$_M$ or BSA$_D$ to colloidal gold at several pH values. The methods of the present invention demonstrate that spectroscopic methods are unable to identify the best conditions for producing homogeneous protein colloidal gold complexes. For example, the absorbance data suggested that adsorption of 150 to 250 μg BSA$_M$/5 ml colloidal gold at pH 6 was slightly better than or equal to adsorption at pH 5.5 and that the adsorption of 150 to 250 μg $BSA_D$/5 ml colloidal gold at pH 5.5 was slightly better than or equal to adsorption at pH 6.0 or pH 7.0. Several of the absorbance values were nearly identical. For example, 250 μg $BSA_M$ adsorbed at pH 5.5 versus 250 μg $BSA_M$ adsorbed at pH 6.0. The absorbance data suggested that these two preparations were nearly equivalent or, in effect, that $BSA_M$-colloidal gold prepared at pH 5.5 would not be much different than $BSA_M$-colloidal gold prepared at pH 6. However, when these samples were compared using agarose electrophoresis their electrophoretic patterns were found to differ markedly.

As shown in FIG. 4, the electrophoretic patterns for $BSA_M$-colloidal gold prepared at pH 6 were elongated while the patterns for $BSA_M$-colloidal gold prepared at pH 5.5 changed from elongated patterns at low protein concentrations to nearly round patterns as the quantity of protein added was increased. In FIG. 4, except for a small trailing portion, $BSA_M$-colloidal gold prepared by the addition of 250 μg $BSA_M$ at pH 5.5 appeared to be the more similar to the electrophoretic pattern, shown in FIG. 9, of the free protein in agarose than $BSA_M$-colloidal gold prepared by the addition of the same quantity of $BSA_M$ at pH 6. Similarly the patterns for $BSA_D$-colloidal gold prepared at pH 6 were elongated even at 250 μg $BSA_D$ while the electrophoretic patterns of $BSA_D$-colloidal gold prepared at pH 5.5 changed from elongated patterns, at low concentrations of $BSA_D$, to nearly round patterns as the quantity of $BSA_D$ increased as shown in FIG. 5. The electrophoretic pattern of $BSA_D$-colloidal gold prepared at pH 5.5 closely resembled the electrophoretic pattern obtained for the unbound protein, and was therefore homogeneous.

The BSA utilized in these experiments was homogeneous as demonstrated by their electrophoretic mobility. i.e., their nearly round electrophoretic patterns following electrophoresis in agarose as shown in FIG. 9. By comparison the elongated patterns obtained for BSA-colloidal gold (pH 6.0), for example, suggested heterogeneity. Two-dimensional electrophoresis was used to demonstrate that the elongated electrophoretic patterns were due to mobility heterogeneity within the BSA-colloidal gold (pH 6.0) samples. This approach has been used previously to demonstrate the presence of faster and slower protein molecules within a given protein population (17). FIG. 8 demonstrate that the fastest subpopulations of BSA-colloidal gold (pH 6.0) continued to migrate the fastest and the slowest subpopulations of BSA-colloidal gold (pH 6.0) continued to migrate the slowest following rotation of the gel by 90°. By comparison the more compact patterns observed for BSA-colloidal gold (pH 5.5) retain much of their compactness in the second direction.

Further, the absorbance data suggested that $BSA_D$-colloidal gold prepared by the addition of 250 μg $BSA_D$ at pH 7 resulted in a product having an absorbance value nearly identical to those produced by the addition of 250 μg $BSA_D$ to colloidal gold at pH 5.5 and pH 6.0. Surprisingly, neither this sample nor any of the samples prepared at pH 7 migrated whatsoever during electrophoresis. These data are disturbing and demonstrate that all protein-colloidal gold preparations should be tested and produced by electrophoresis. Those which fail to exhibit electrophoretic characteristics similar or identical to those exhibited by the native but unbound protein are in fact heterogenous and unsuitable. The failure of rabbit anti-BSA, an polyclonal antisera, to agglutinate $BSA_D$-colloidal gold prepared at pH 7 support this conclusion.

It was recently suggested (18) that colloidal gold could be stabilized at any pH value more alkaline than its pI, provided that a sufficient quantity of protein was added. However, as demonstrated herein, $BSA_D$ could be used to stabilize colloidal gold at pH 7.0 as indicated by the coagulation curves, but the product did not react detectably with antibody to BSA and the $BSA_D$-colloidal gold complex did not exhibit homogeneous electrophoretic pattern like that of native BSA. Thus, stabilization by itself was not a reliable indicator for selection of the conditions which might be used in the production of homogeneous BSA-colloidal gold complexes.

It was also reported (18) that protein-colloidal gold complexes formed aggregates when stored at pH values near the pI of the protein. As a result, it appeared that protein-colloidal gold complexes should be prepared at pH values where the complexes are most stable. Thus, human serum albumin was stable at pH values from pH 6-10. HSA appears to yield electrophoretic data similar to that of BSA (11). Homogeneous BSA-colloidal gold complexes Were prepared at pH 5.5 but not at pH 6, 7, 8 or 9. Based upon the results obtained herein, it appears that the storage pH of protein-colloidal gold complexes should be adjusted following adsorption of the protein to the colloidal gold and that the best storage pH should not determine the pH of adsorption. This appears to be supported by other research (18) data which demonstrated that aggregation was not necessarily a rapid event. No aggregation of HSA-colloidal gold was detected during storage at pH 5.5 for approximately one hour. Thus, it would appear to be better to adsorb protein at a pH value yielding the most homogeneous product and then to adjust the storage conditions, e.g., pH, buffer and electrolyte concentrations, addition of anti-aggregation substances such as protein or polymer. Electrophoresis has long been utilized in evaluating protein purity and heterogeneity. Immunoelectrophoresis in particular has taken advantage of the electrophoretic mobility of proteins obtained at alkaline pH values. At pH 8.6 most serum proteins exhibit a negative charge and migrate towards the positively charged anode. Some proteins, such as albumin, exhibit a homogeneous, discrete electrophoretic pattern in agarose, e.g., they migrate as a small round spot, while other proteins exhibit a more elongated heterogenous pattern.

Electrophoresis in agar and agaroses having charged groups results in an electroendosmotic effect, a liquid flow towards the cathode (17). This flow enhanced separations of serum proteins and made their visualization with antisera a valuable technique in immunology. More recently, agarose gels which exhibit no detectable electroendosmotic flow have been produced. Both types of agarose have been used in the examples presented herein.

The data obtained in FIGS. 4 and 5 were obtained using 1% agarose having an electroendosmotic value of 0.13. The data obtained in FIGS. 5 and 6 were obtained using 1% IsoGel agarose having an electroendosmotic value of approximately zero. As demonstrated in FIG. 9, BSA migrates farther towards the anode in 1% Iso-Gel (FIG. 9 Panels C and D), than in the other agarose (FIG. 9 Panels A and B). A small but noticeable effect on the shape of the electrophoretic pattern was also observed when BSA-colloidal gold was electrophoresed in 1% IsoGel agarose the distance of migration increased and none of the homogeneous preparations migrated toward the cathode. Preparations of BSA-colloidal gold adsorbed at pH 7, 8 or 9 migrated a short distance towards the anode (FIG. 6 and 7). The latter preparations did not agglutinate with antibody to BSA. The failure of these preparations to agglutinate during passive gold agglutination suggests that either no BSA was adsorbed at these pH values, that the quantity adsorbed was insufficient for detection by this procedure, that the antigenic sites became denatured following adsorption, or that the orientation of BSA on the gold particles did not favor reactivity with the polyclonal rabbit antiserum.

The electrophoretic mobility of a particle in agarose is determined by the surface net charge density and by retardation of the particle migration according to size (19). Thus a uniform electrophoretic pattern for a given protein-colloidal gold complex similar to that of the unbound protein would suggest that the protein-colloidal gold preparation contained colloidal gold particles which had adsorbed a similar number of protein molecules. The adsorption of fewer or more protein molecules would most likely result in a different net charge density which would be observed as a longer pattern. Accordingly, those particles which migrate as a discrete spot or fraction through the electrophoretic medium are homogeneous.

The literature suggests that some conditions, e.g., pH and concentration, lead to the production of more heterogeneity in complexes than others. Previously, however, no method was available which permitted one to readily compare and recognize the presence of protein-colloidal gold complex heterogeneity and to select conditions resulting in the production of maximal protein-colloidal gold complex homogeneity.

In a further example, commercially produced protein-colloidal gold preparations were purchased from three companies; Sigma Chemical Co., St. Louis, Mo.; Zymed Laboratories, San Francisco, Calif.; Janssen Life Sciences, Olen, Belgium (distributed by Amersham Corporation, Arlington Heights, Ill.). These samples were selected because each of the proteins involved may be obtained in relatively pure form such that they are electrophoretically homogeneous, e.g., they migrate as a small discrete spot in agarose.

Sigma Chemical Co:
  Albumin-Biotin 76F-8010)
  Protein A-colloidal gold (Lot 68F-8010)
  Protein G-colloidal gold (Lot 38F-8040)
Zymed Laboratories:
  Albumin-colloidal gold (Lot 90603189)
  Protein A-colloidal gold (Lot 90803490)
  Protein G-colloidal gold (Lot 90803382)
Janssen Life Sciences:
  Protein A-colloidal gold (Lot 09F-223)
  Protein G-colloidal gold (Lot 09E-251)

Each of these preparations were electrophoresed for 1 hour at 200 volts in 1% agarose in 0.02M tris, 0.006M tricine, 0.027 g calcium lactate $5H_2O$ pH 8.6. The results indicated that the Sigma products exhibited the poorest mobility in agarose migrating only 1-2 millimeters or not at all. These mobilities were much different than the native protein electrophoresed under identical conditions. The Zymed products migrated about 6 mm in agarose but each sample contained a long tail connecting the main portion of each sample to the starting well. The Janssen samples migrated 6-9 mm followed by a long tail connecting or nearly connecting each sample to the starting well. These results were reproduced in three separate electrophoretic experiments. Accordingly, none of the commercially available products tested were homogeneous. Therefore, experimental results using these products could not be predicted, relied on, or reproduced.

Recombinant protein G (Gammabind, Genex) was adsorbed to colloidal gold over a series of pH values (pH 5.0, 5.5, 6.0, 6.5, and 7.0); protein concentrations of 5-50 $\mu$g were used. The data demonstrate that both the pH of adsorption and the quantity of recombinant protein G added to colloidal gold could be varied to produce recombinant protein G-colloidal gold complexes which exhibited homogenous electrophoretic mobilities. The most homogenous products were obtained at pH 5.0 and 50 $\mu$g recombinant protein G per 5 ml of colloidal gold. The electrophoretic mobility of the recombinant protein G-colloidal gold was similar to that observed for the unbound protein. Analogous experiments concerning protein A are in progress.

Figure 10:
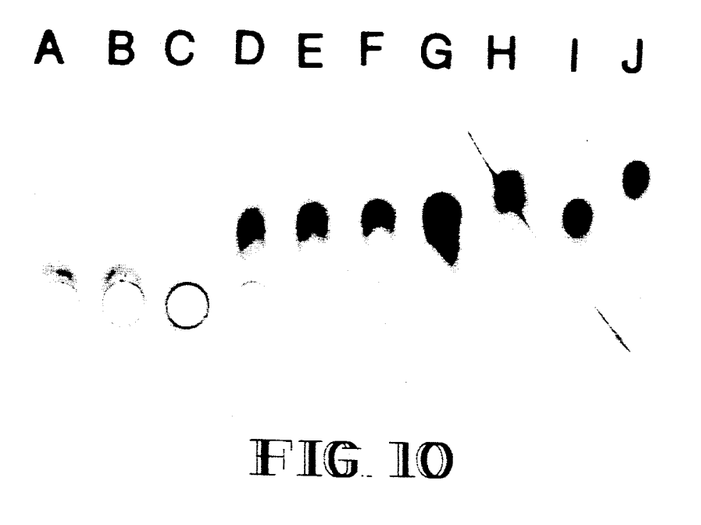
FIG. 10 is a photograph of the one dimensional gel electrophoresis of 9 commercial samples and one sample (J) prepared according to the present invention for comparison. A is Sigma albumin-biotin-colloidal gold; B is Sigma protein A-colloidal gold; C is Sigma protein G-colloidal gold; D is Zymed albumin-colloidal gold; E is Zymed protein A-colloidal gold; F is Zymed protein G-colloidal gold; G is Janssen protein A-colloidal gold; H is Janssen protein G-colloidal gold; I is recombinant protein G-colloidal gold prepared through initial steps of the present invention; J is $BSA_D$-colloidal gold. Note that all of the samples except J have trailing material and are therefore electrophoretically heterogenous.

FIG. 10 shows the results of the one dimensional gel electrophoresis of 9 commercial samples and one sample (J) prepared according to the present invention for comparison. A is Sigma albumin-biotin-colloidal gold; B is Sigma protein A-colloidal gold; C is Sigma protein G-colloidal gold; D is Zymed albumin-colloidal gold; E is Zymed protein A-colloidal gold; F is Zymed protein G-colloidal gold; G is Janssen protein A-colloidal gold; H is Janssen protein G-colloidal gold; I is recombinant protein G-colloidal gold prepared through initial steps of the present invention; J is $BSA_D$-colloidal gold. Note that all of the samples except J have trailing material (greater than about 33%) and are therefore electrophoretically heterogenous.

Figure 11:
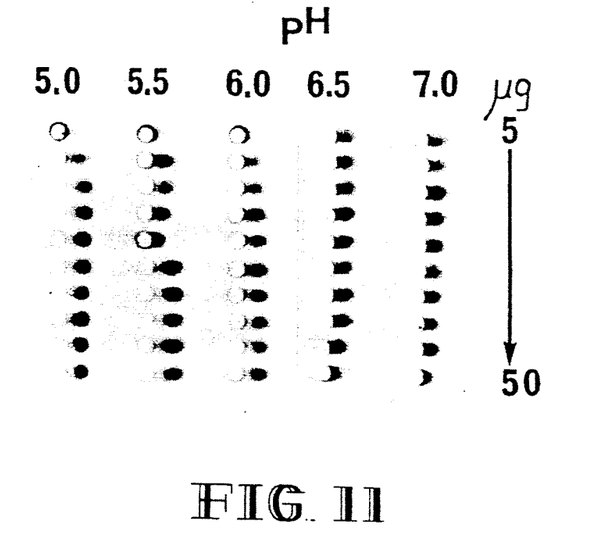
FIG. 11 is a copy of a one dimensional gel electrophoresis of recombinant protein G-colloidal gold. The recombinant protein G was added in 5 μg increments from 5 to 50 μg per 5 ml of colloidal gold adjusted to one of five different pH values; pH 5.0, 5.5, 6.0, 6.5, 7.0.

FIG. 11 shows results of a one dimensional gel electrophoresis of recombinant protein G-colloidal gold. The recombinant protein G was added in 5 $\mu$g increments from 5 to 50 $\mu$g per 5 ml of colloidal gold adjusted to one of five different pH values; pH 5.0, 5.5, 6.0, 6.5, 7.0.

While the invention is susceptible to various modifications and alternative forms, specific embodiments thereof has been shown by way of example and have been described herein in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Specific reference is made to copending application Ser. No. 07/501,534, filed Mar. 28, 1990, which is incorporated by reference herein. The following publications are incorporated by reference for the reasons herein cited.

1. Horisberger M, Russet J, Bauer H. Colloidal gold granules as markers for cell surface receptors in the scanning electron microscope. Experientia 1975; 31:1147.

2. Geoghegan WD, Ackerman. Adsorption of horseradish peroxidase, ovomucoid and anti-immunoglobulin to colloidal gold for the indirect detection of concanavalin A, wheat germ agglutinin and goat anti-human immunoglobulin on cell surfaces at the electron microscopic level: a new method, theory and application. J. Histochem. Cytochem 1977; 25:1187.

3. Geoghegan WD, Ambegaonkar S, Calvanico N. Passive gold agglutination. An alternative to passive hemagglutination. J. Immunol. Methods 1980; 34:11.

4. Surek B, Latzko E. Visualization of antigenic proteins blotted onto nitrocellulose using the immuno-gold-staining (IGS) method. Biochem. Biophys. Res. Comm. 1984; 121:284.

5. Brada D, Roth J. Golden blot-detection of polyclonal and monoclonal antibodies bound to antigens on nitrocellulose by protein A-gold complexes. Anal. Biochem. 1984; 142:79.

6. Hsu YH. Immunogold for detection of antigen on nitrocellulose paper. Anal. Biochem. 1984; 142:142.

7. Moeremans M, Dansels G, van Dijck A, et al. Sensitive visualization of antigen-antibody reactions in dot and blot immune overlay assays with immunogold and immunogold/silver staining. J. Immunol. Methods 1984; 74:553.

8. Garland JM. Preparation and performance of gold-labeled concanavalin A for the location of specifically reactive sites in walls of S faecalis 8191. In E Wisse, Wth Daems, I Molenarr, P van Duijn, eds. Electron Microscopy nd Cytochemistry. Amsterdam: North Holland 1971:303.

9. Slot JW, Geuze HJ. Sizing of protein A-colloidal gold probes for immunoelectron microscopy. J. Cell Biol. 1981; 90:533.

10. Geoghegan WD. The effect of three variables on adsorption of rabbit IgG to colloidal gold. J. Histochem Cytochem 1988; 36:401.

11. Geoghegan WD. The electrophoretic mobility of protein colloidal gold complexes. J. Histochem Cytochem (abstract) 1989; 37:939.

12. Roth J, Bendayan M, Orci L. Ultrastructural localization of intracellular antigens by the use of protein A-gold complex. J. Histochem. Cytochem. 1978; 26:1074.

13. Horisberger M, Rosset J. Colloidal gold, a useful marker for transmission and scanning electron microscopy J Histochem Cytochem. 1977; 25:295.

14. Habeeb AFSA. lmmunochemistry of bovine serum albumin. In Atassi MZ, ed. Immunochemistry of Protein. New York: Plenum Press 1977; 3:233.

15. Janatova J, Fuller JK, Hunter MJ. The heterogeneity of bovine albumin with respect to sulfhydryl and dimer content. J. Biol. Chem. 243; 3612:1968.

16. Monthony JF, Wallace EG, Allen DM. A non-barbital buffer for immunoelectrophoresis and zone electrophoresis in agarose gels. Clin Chem 1978; 24:1825.

17. Wieme RJ. Agar Gel Electrophoresis. New York: Elsevier, 1965.

18. Park K. Factors affectig efficiency of colloidal gold staining: pH-dependent stability of protein-gold conjugates. Scanning Microscopy 1989; Supplement 3:15.

19. Tietz D. Gell electrophoresis of intact subcellular particles. J. Chromat. 1987; 418:305.

What is claimed is:

1. A method for defining reaction conditions producing a homogeneous protein-colloidal gold complex, the method comprising:
   (a) reacting colloidal gold particles with a protein at a series of protein concentrations between 10 $\mu$g/ml and 500 $\mu$g/ml and at various pH values between 5.0 and 7.0 to produce a set of protein-colloidal gold complex suspensions; and
   (b) electrophoretically analyzing samples of said suspensions on a gel to identify reaction conditions of pH and protein concentration resulting in homogeneity, said homogeneity being defined as the protein-colloidal gold complexes having a uniform size, shape, charge, and ratio of size to charge.

2. A method for producing a homogeneous protein-colloidal gold complex, the method comprising:
   (a) reacting colloidal gold particles with a protein at a series of protein concentrations between 10 $\mu$g/ml and 500 $\mu$g/ml and at various pH values between 5.0 and 7.0 to produce a set of protein-colloidal gold complex suspensions;
   (b) electrophoretically analyzing samples of said suspensions on a gel to identify reaction conditions of pH and protein concentration resulting in homogeneity, said homogeneity being defined as the protein-colloidal gold complexes having a uniform size, shape, charge, and ratio of size to charge; and 3. The method of claim 2 where in step (b) one-dimensional particle gel electrophoresis is used for electrophoretic analysis of said sample.

4. The method of claim 2 where in step (b) two-dimensional particle gel electrophoresis is used for electrophoretic analysis of said sample.

5. The method of claim 2 wherein said protein is selected from the group consisting of monomeric BSA, dimeric BSA, monomeric HSA, dimeric HSA, protein-A and protein G.

6. The method of claim 2 wherein said protein is an antigen or an antibody.

7. The method of claim 2 wherein the concentration of said protein is from 75 to about 250 micrograms/ml.

8. The method of claim 2 wherein said pH is from about 5.5 to about 6.0.

9. A method for producing a homogeneous BSA-colloidal gold complex, the method comprising:
   (a) reacting colloidal gold particles with BSA at a series of BSA concentrations between 75 $\mu$g/ml and 250 $\mu$g/ml and at various pH values between 5.0 and 7.0 to produce a set of BSA-colloidal gold complex suspensions;
   (b) electrophoretically analyzing samples of said suspensions on a gel to identify reaction conditions of pH and BSA concentration resulting in homogeneity, said homogeneity being defined as the protein-colloidal gold complexes having a uniform size, shape, charge, and ratio of size to charge; and
   (c) reacting homogeneous BSA and colloidal gold under the conditions identified in step (b).

10. The method of claim 9 wherein the pH is about 5.5 and the concentration of a homogeneous BSA is about 250 micrograms/ml.

11. A protein-colloidal gold complex migrating through an electrophoretic medium as a substantially symmetrical spot.

12. The composition of claim 11 wherein said composition migrates as a substantially symmetrical spot during one-dimensional particle gel electrophoresis.

13. The composition of claim 11 wherein said composition migrates as a substantially symmetrical spot during two-dimensional particle gel electrophoresis.

14. A BSA-colloidal gold complex formed from colloidal gold particles migrating through an agarose electrophoretic medium at a constant voltage of about 200 volts for an about 8.3×10.2 cm gel as a substantially symmetrical spot.

15. A HSA-colloidal gold complex formed from colloidal gold particles migrating through an agarose electrophoretic medium at a constant voltage of about 200 volts for an about 8.3×10.2 cm gel as a substantially symmetrical spot.

16. The method of claim 1, 2 or 9 wherein the colloidal gold particles are at a concentration which has an absorbance of about 0.90 at 525 nanometers.

17. A homogeneous protein-colloidal gold complex produced by the method of claim 2.

* * * * *